United States Patent [19]
Calvo Salve et al.

[11] Patent Number: 5,843,509
[45] Date of Patent: Dec. 1, 1998

[54] STABILIZATION OF COLLOIDAL SYSTEMS THROUGH THE FORMATION OF LIPID-POLYSSACHARIDE COMPLEXES

[75] Inventors: Pilar Calvo Salve; Maria Jose Alonso Fernandez; Carmen Remunan Lopez; Jose Luis Vila Jato, all of Santiago de Compostela, Spain

[73] Assignee: Universidade de Santiago de Compostela, Spain

[21] Appl. No.: 776,507

[22] PCT Filed: May 24, 1996

[86] PCT No.: PCT/ES96/00116

§ 371 Date: Feb. 27, 1997

§ 102(e) Date: Feb. 27, 1997

[87] PCT Pub. No.: WO96/37232

PCT Pub. Date: Nov. 28, 1996

[30] Foreign Application Priority Data

May 26, 1995 [ES] Spain ..................................... 9501035

[51] Int. Cl.$^6$ ................. A61K 9/16; A61K 9/14
[52] U.S. Cl. .......................... 424/489; 424/490; 424/491; 424/493; 424/497; 424/498; 514/937; 514/963
[58] Field of Search ..................... 424/450, 489, 424/490, 493, 497, 498; 514/937–943, 963

[56] References Cited

U.S. PATENT DOCUMENTS 5,536,508  7/1996  Canal et al. ............................ 424/501

FOREIGN PATENT DOCUMENTS 0486959  5/1992  European Pat. Off. .
864032   5/1986  South Africa .
93 18852 9/1993  WIPO .

OTHER PUBLICATIONS

P. Faldt, et al., "Stabilization by chitosan of soybean oil emulsions coated with phospholipid and glycocholic acid", *Colloids Surfaces A: Physicochem. Eng. Aspects,* 71, 187–195, 1993.

I. Henriksen, et al., "Interactions between liposomes and chitosan", *Int. J. Pharm.,* 101, 227–236, 1994.

Faldt, P. et al. "Stabilizatoin by chitosan of soybean oil emulsions coated with phospholipid and glycocholic acid" (1993) Colloids and Surfaces A: Physicochemical and Engineering Aspects, vol. 71, pp.: 187–195, complete document.

*Primary Examiner*—Gollamudi S. Kishore
*Attorney, Agent, or Firm*—Ostrolenk, Faber, Gerb & Soffen, LLP

[57] ABSTRACT

Stabilization of colloidal systems through the formation of lipid-polyssacharide complexes. Development of a procedure for the preparation of colloidal systems involving a combination of two ingredients: a water soluble and positively charged polyssacharide and a negatively charged phospholipid. Colloidal systems (submicron emulsions and polymeric nanoparticles and nanocapsules) are stabilized through the formation, at the interface, of an ionic complex: aminopolyssachride-phospholipid. These colloidal systems are characterized by their positive charge and their improved stability. Furthermore, they can be freeze-dried, stored in a dry state and hydrated when required. They can be interesting systems for the administration of drugs by the oral, transdermal, ocular, nasal and vaginal routes of administration. In addition, they can be of interest for cosmetic use.

20 Claims, No Drawings

STABILIZATION OF COLLOIDAL SYSTEMS THROUGH THE FORMATION OF LIPID-POLYSSACHARIDE COMPLEXES

This application is a 371 of PCT/ES96/00116 filed May 24, 1996.

This invention relates to stabilization of colloidal systems through the formation of lipid-polyssacharide complexes and development of a procedure for the preparation of colloidal systems involving a combination of two ingredients: a water soluble and positively charged polyssacharide and a negatively charged phospholipid. The procedure can be applied to the stabilization of colloidal systems of pharmaceutical and cosmetic use. These systems include oil-in-water submicron emulsions, nanocapsules consisting of an oily core surrounded by a polymer coating and polymeric solid nanoparticles. The common feature to all these colloidal systems is that they consist of a dispersed phase—oily nanodroplets, nanocapsules or nanoparticles—and a continuous aqueous phase. The originality of the procedure relies on the incorporation of lecithin (anionic ingredient), as a lipophilic surfactant, in the dispersed phase and of the chitosan, as a hydrophilic suspending agent, in the continuous aqueous phase.

Lecithin is a natural surfactant composed of a mixture of various phospholipids. The major compound is phosphatidylcholine (a phospholipid of a neutral character) and the secondary compounds are phosphatidylethanolamine, phosphatidylserine and phosphatidic acid (phospholipids with a negative charge). Presently, there are several types of lecithin available in the market. They differ in their origin and in their phosphatidylcholine content.

Chitosan is a natural polymer obtained by a deacetatilation process of the chitin (compound extracted from the crustacean shells). Chitosan is an aminopolyssachride and has a positive charge. Presently, there are several types of chitosan available in the market. They differ in their molecular weight, deacetilation degree and the type of salt or acid form.

The colloidal systems of the invention are characterized by having contain lecithin and chitosan in their composition and they have a positive charge and an improved stability. Other ingredients will be specific to the type of system i.e. an oil, in the case of the submicron emulsions; an oil and a hydrophobic polymer, in the case of the nanocapsules, and a hydrophobic polymer in the case of the nanoparticles. Drugs, proteins and other bioactive compounds of interest in medicine and cosmetics can be incorporated in these systems. Consequently, the application of these systems could be extended to the fields of medicine and cosmetics.

A important draw back of the colloidal carriers is their unstability following in vivo administration and also during storage. It is well known that the majority of the colloidal carriers have a negative surface charge and, because of this fact, they interact with the cationic biologic compounds upon in vivo administration, thus leading to coalesce and destruction of the system. Difficulties in the freeze-drying process, more specifically problems in the reconstitution of the freeze-dried systems, represent another important limitation for the correct exploitation of the colloidal systems specially the nanocapsules and submicron emulsions. As a consequence, these systems have to be stored as a suspension liquid form, a situation that normally leads to the destruction of the systems in a few months. The novel systems presented here have a positive charge and an improved stability upon contact with biological cations and during storage. Consequently, these systems overcome the limitations mentioned above.

There are in the literature a large number of publications and patents describing procedures to produce colloidal systems such as nanoparticles, nanocapsules and submicron emulsions. Therefore, the production of these systems is not the object of the present invention. The object is, however, the incorporation in such colloidal systems of two specific ingredients: lecithin and chitosan. The preparation of these systems involves the use of two phases: an oily phase that is dispersed in an aqueous phase. Both phases normally contain surfactants. The most common surfactant introduced in the oily phase is lecithin. Lecithins are natural compounds that contain phosphatidylcholine and other phospholipids of negative charge. Consequently, colloidal systems containing lecithin have a more or less important negative surface charge. This negative charge normally leads to the destruction of the system, mainly upon contact with biological cations. This limitation inherent to most of the colloidal systems has been recently overcome by using lipophilic surfactants with a positive charge. These positive surfactants are introduced in the dispersed oily phase (S. Benita, oil-in water emulsion of positively charged particles WO 93/18852).

The present invention describes a new approach to provide the colloidal particles of a positive charge. This approach is based on the use of the cationic polyssacharide, chitosan, that is dissolved in the continuous aqueous phase and a lipid anionic surfactant, such as lecithin, that is introduced in the oily dispersed phase. The positively charged chitosan molecules interact with the negatively charged phospholipids, thus forming a film at the interface of the colloidal system. The interaction process of chitosan with phospholipids was previously described as a way to stabilize emulsions (no submicron emulsions) ( P. Faldt, B. Bergenstahl, P.M. Claesson, Stabilization by chitosan of soybean oil emulsions coated with phospholipid and glycolic acid, Colloids Surfaces A: *Physicochem. Eng. Aspects* 71, 187–195, 1993) and liposomes (I. Henriksen, G. Smistad and J. Karlsen, Interactions between liposomes and chitosan, *Int. J. Pharm.*, 101, 227–236, 1994). Nevertheless, no reference concerning the application of such interaction (chitosan-phospholipid) to the stabilization of submicron emulsions, nanocapsules and nanoparticles has been found. On the other hand, it is important to mention that the approaches described until now for the freeze-drying of colloidal systems, such as nanocapsules and submicron emulsions, are based on the use of enormous amounts of sugars (R. J. Gautier and R. S. Levinson, Lyophilized emulsion compositions and method, South Africa patent No. 864032) whereas the freeze drying of the nanocapsules covered in this invention require the use of relatively low amounts of sugars (less than 10%).

The systems covered herein, characterized by the formation of a polysaccharidelipid complex at the interface, have some relevant advantages: (1) The systems can be stored in a suspension liquid form for extended periods of time, (2) the nanocapsules based on this approach can be freeze dried and the resultant dry product reconstituted upon addition of water (3) the chitosan-coated nanocapsules herewith described are more stable in the presence of biological cations than conventional uncoated nanocapsules, (4) the systems have a positive electrical surface charge that enables their interaction with negatively charged biological surfaces.

The present invention describes novel systems of interest in therapeutics and cosmetics. These systems can be presented in a liquid form of variable viscosity or in a semi-solid (cream) or solid form (freeze-dried powder).

The dispersed phase of the system consists either of a polymer or an oil or both substances simultaneously. The specific ingredient of this dispersed phase is a negatively charged phospholipid. This phase can contain as well a variable amount of an active ingredient. The oils can be chosen among vegetable oils or semisynthetic polyoxyethylenated oils (Migliol®, Labrafil®, Labrafac® . . . ) of various H.L.B. (hydrophilic lipophilic balance) values. The polymer can be any hydrophobic polymer which is adequate for pharmaceutical or cosmetic use. The proportion of the hydrophobic polymer with respect to the oily phase can vary from 0% (submicron emulsions) up to 100% (nanoparticles). Intermediate proportions lead to the formation of nanocapsules in which the oil is in the polymer forming a reservoir system.

The specific ingredient of the external aqueous phase is chitosan. For freeze drying purposes some cryoprotective agents such as dextran and glucose need to be added to this external phase. This phase can incorporate as well ingredients to provide a certain density or viscosity to the preparation, bacteriostatic agents for the prevention of contamination and other hydrophilic agents.

These systems can be formulated in different ways in order to incorporate in their structure one or more active ingredients of a hydrophilic or lipophilic character. The active ingredient is the ingredient for which the formulation is destined; in other words, the ingredient which will have an effect following its administration to an organism (humans or animals). The corresponding effect can be curing, minimizing or preventing a disease (drugs, vitamins, vaccines . . . ) or improving the physical appearance and aesthetics (e.g . . . skin hydration . . . ) and others.

Cyclosporin A, an immunossupressive peptide, indomethacin (anti-inflammatory drug) metipranolol (beta-blocker) and tiopental (hypnotic agent) are examples of drugs which have been successfully associated to the colloidal systems described herein.

A common feature to the systems described herein is the colloidal nature, which means that their size is lower that 1 $\mu$m. Tables 1 and 2 show the mean particle size of the nanocapsules, submicron emulsions and nanoparticles containing the oil Migliol® 840 and various amounts of polyepsiloncaprolactone, soybean lecithin and dextran.

As mentioned above, a relevant property of the systems described here is their positive electrical charge. This positive charge promotes the interaction of the systems with the negatively charged mucosa and epithelia and also improves their stability in the presence of biological cations. As shown in table 3, the zeta potential of the systems varies between +30 and +60 mV, being these values dependent on the molecular weight of chitosan.

The inner structure of the systems described here is variable and dependent upon the composition of the system. As indicated before, the composition of the systems can vary substantially, the common ingredients being lecithin and chitosan or their derivatives. Two main inner structures can be described: a reservoir system consisting of an oily core surrounded or not by a polymer wall and a matrix system consisting of solid particles containing none or little amounts of oil entrapped.

The redispersability of the colloidal systems upon freeze-drying is a major advantage of the systems. Tables 3 and 4 show the particle size of the nanocapsules before and after freeze-drying.

The procedure described in this invention leads to the formation of novel systems for pharmaceutical or cosmetic applications. In addition, these systems could be administered by various routes: topical, oral, nasal, pulmonary, vaginal and subcutaneous. The specific ingredients, chitosan and lecithin, provide to these systems a positive electrical charge and an improved stability, not only during storage but also upon freeze-drying and further rehydration.

TABLE 1

Particle size of the poly($\epsilon$-caprolactone) (PECL) nanocapsules containing Migliol ® 840 and a fixed concentration of chitosan (Seacure 123, 0.2%)

| % Lecithin (w/v) | % Dextran (w/v) | % PECL (w/v) | | |
|---|---|---|---|---|
| | | 0 | 1 | 2 |
| 0.5 | 1 | 340 ± 23 | 361 ± 22 | 353 ± 21 |
| 0.5 | 2 | 278 ± 43 | 324 ± 28 | 292 ± 38 |
| 1 | 1 | 324 ± 23 | 384 ± 5 | 313 ± 19 |
| 1 | 2 | 313 ± 11 | 303 ± 28 | 318 ± 24 |
| 1.5 | 1 | 314 ± 19 | 341 ± 18 | 346 ± 20 |
| 1.5 | 2 | 284 ± 12 | 321 ± 10 | 339 ± 13 |

TABLE 2

Particle size of the poly($\epsilon$-caprolactone) (PECL) nanoparticles prepared with a fixed concentration of chitosan (Seacure 223, 0.2%)

| % Lecithin (w/v) | % Dextran (w/v) | % PECL (w/v) | |
|---|---|---|---|
| | | 1 | 2 |
| 0.5 | 1 | 290 ± 16 | 308 ± 15 |
| 0.5 | 2 | 286 ± 12 | 296 ± 20 |
| 1 | 1 | 330 ± 15 | 330 ± 2 |
| 1 | 2 | 299 ± 16 | 317 ± 10 |
| 1.5 | 1 | 337 ± 10 | 355 ± 19 |
| 1.5 | 2 | 326 ± 18 | 332 ± 12 |

TABLE 3

Zeta potential of the poly($\epsilon$-caprolactone) (PECL) nanocapsules and submicron emulsions containing Migliol ® 840 and a fixed concentration of chitosan (Seacure 320, 0.2%).

| % Lecithin (w/v) | Zeta Potential (mV) | | |
|---|---|---|---|
| | Submicron emulsions | Nanocapsules | |
| | | PECL 1% | PECL 2% |
| 0.5 | +52 ± 2 | +60 ± 1 | +60 ± 1 |
| 1 | +60 ± 1 | +61 ± 1 | +60 ± 0.07 |
| 1.5 | +59 ± 0.3 | +59 ± 2 | +61 ± 0.4 |

TABLE 4

Particle size of the poly($\epsilon$-caprolactone) (PECL) nanocapsules containing Migliol ® 840 and a fixed concentration of chitosan (Seacure 223 viscosity 100 cps and Seacure 320 viscosity 680 cps, 0.2%). Final concentration of PECL and lecithin in the suspension: 1% and 0.5% respectively.

| Chitosan viscosity (cps) | % Dextran (p/v) | Particle size (nm) | |
|---|---|---|---|
| | | Before freeze-drying | After freeze-drying |
| 100 | 1 | 459 ± 23 | 487 ± 19 |
| 100 | 2 | 472 ± 8 | 462 ± 19 |
| 680 | 1 | 443 ± 30 | 475 ± 30 |
| 680 | 2 | 461 ± 13 | 505 ± 16 |

EXAMPLE 1

Preparation of a formulation of nanocapsules containing PECL and Migliol® 840.

The nanocapsules were prepared using the following ingredients (%,w/w):

| | |
|---|---|
| Migliol ® 840 oil | 0.5 |
| Soybean lecithin | 1.0 |
| polyepsiloncaprolactone | 1.0 |
| Dextran | 1.0 |
| Chitosan | 0.2 |
| Water | up to 100% |

Chitosan and dextran were dissolved in an acidic aqueous solution (acetic acid 0.05M, pH5.0). The oil Migliol® 840, the surfactant soybean lecithin and the polymer poly(ε-caprolactone) were dissolved in 25 ml of acetone. The acetonic solution was then added, upon magnetic agitation, to an aqueous solution. Three minutes later the system was transferred to a rotavapor for the elimination of the acetone. The size and zeta potential of the nanocapsules were: 385 nm and +45 mV respectively.

Finally, glucose was dissolved in the aqueous suspending medium and the nanocapsules freeze-dried. The particle size and zeta potential of the nanocapsules was determined again upon freeze-drying and resuspension. Results were: 359 nm and +42 mV.

EXAMPLE 2

Preparation of a formulation of nanocapsules containing PECL and Migliol® 840.

The nanocapsules were prepared as described in example 1 but containing different amounts of lecithin and oil:

| | |
|---|---|
| Migliol ® 840 oil | 1.5 |
| Soybean lecithin | 0.5 |
| polyepsiloncaprolactone | 1.0 |
| Dextran | 1.0 |
| Chitosan | 0.2 |
| Water | up to 100% |

The particle size and zeta potential of these nanocapsules were: 433 nm and +32 mV, respectively, before freeze-drying and 582 and +43 mV after freeze-drying.

EXAMPLE 3

Preparation of a formulation of a submicron emulsion containing Migliol® 840.

The emulsion was prepared as described in example 1 but without the polymer PECL:

| | |
|---|---|
| Migliol ® 840 oil | 1.5 |
| Soybean lecithin | 0.5 |
| Dextran | 1.0 |
| Chitosan | 0.2 |
| Water | up to 100% |

The results of particle size and zeta potential were: 463 nm and +42 mV, respectively.

We claim:

1. A process for the preparation of a colloidal system having a size less than 1 micron suitable for delivery of an active material, said system comprising a coated member selected from the group consisting of nanodroplet, nanocapsule and nanoparticle, comprising the steps of providing a solution comprising hydrophobic polymer or oil and negatively charged phospholipid dissolved in an organic solvent, providing an aqueous solution of cationic aminopolyssacharide selected from the group consisting of chitin and chitosan, combining said organic and aqueous solutions so as to simultaneously and spontaneously form and coat said member with a film which is the ionic reaction product of said phospholipid and aminopolyssacharide, and to provide said particles with a positive surface charge wherein one of said solutions contains said active material and wherein said amino- polyssacharide is between 0.05 and 0.5% by weigh and said phospholipid is between 0.2 and 1% by weight.

2. The process of claim 1, wherein said phospholipid is lecithin.

3. The process of claim 2, wherein said aminopolyssacharide is up to 2% of the mixed organic and aqueous solutions and said phospholipid is up to 5% of said mixed organic and aqueous solutions.

4. The process of claim 2, wherein said aminopolyssacharide is chitosan.

5. The process of claim 2, wherein said hydrophobic polymer or oil is oil in a concentration of up to 1% based on said aqueous medium.

6. The process of claim 5, wherein said oil is selected from the group consisting of vegetable oil and semisynthetic polyoxyethylated oil.

7. The process of claim 2, wherein said hydrophobic polymer or oil is a polyester at a concentration of up to 4%.

8. The process of claim 2, wherein said mixture contains a cyroprotective agent and said particles are freeze dried.

9. The process of claim 8, wherein said cyroprotective agent is dextran or glucose or a mixture thereof.

10. The process of claim 2, wherein said aqueous solution is an aqueous acidic solution.

11. The process of claim 2, wherein said mixing takes places in the presence of an active material selected from the group consisting of drug, vitamin, vaccine and skin hydration agent.

12. The process of claim 11, wherein said active compound is selected from the group consisting of indomethacin, metipranolol, diazepam, tiopental and cyclosporin A.

13. A colloidal system having a size less than 1 micron comprising a coated member selected from the group consisting of nanodroplet, nanocapsule and nanoparticle comprising a hydrophobic polymer or oil and having a surface coating which is the ionic reaction product of a negatively charged phospholipid and a cationic aminopolyssacharide selected from the group consisting of chitin and chitosan, said member having a positive surface charge.

14. The system of claim 13, wherein said phospholipid is lecithin and said aminopolyssacharide is chitosan.

15. The system of claim 14 containing an active material selected from the group consisting of drug, vitamin, vaccine and skin hydration agent.

16. The system of claim 14, in which said member is a nanodroplet.

17. The system of claim 14, which is a nanocapsule.

18. The system of claim 14, which is a nanoparticle.

19. The system of claim 14, containing a cyroprotective agent.

20. A freezed dried system of claim 13.

* * * * *